United States Patent
Lualdi (12) 
(10) Patent No.: US 12,257,706 B2
(45) Date of Patent: Mar. 25, 2025

(54) ROBOTIC WORKING LINE FOR THE PRODUCTION OF CUTTING BODIES, CUTTING BODY AND RELATED WORKING METHOD

(71) Applicant: HPF S.R.L., Fagagna (IT)

(72) Inventor: Gabriele Lualdi, Fagagna (IT)

(73) Assignee: HPF S.R.L., Fagagna (IT)

( * ) Notice: Subject to any disclaimer, the term of this patent is extended or adjusted under 35 U.S.C. 154(b) by 187 days.

(21) Appl. No.: 17/396,637

(22) Filed: Aug. 6, 2021

(65) Prior Publication Data

US 2022/0040848 A1   Feb. 10, 2022

(30) Foreign Application Priority Data

Aug. 6, 2020   (IT) .................. 102020000019411

(51) Int. Cl.
*B25J 9/00*    (2006.01)
*B23K 26/08*   (2014.01)
(Continued)

(52) U.S. Cl.
CPC ......... *B25J 9/0084* (2013.01); *B23K 26/0884* (2013.01); *B25J 9/0093* (2013.01);
(Continued)

(58) Field of Classification Search
CPC combination set(s) only.
See application file for complete search history.

(56) References Cited

U.S. PATENT DOCUMENTS 10,646,696 B2 *   5/2020   Barrish ............. A61M 25/0155
10,737,073 B2 *   8/2020   Barrish ............. A61M 25/0155
(Continued)

FOREIGN PATENT DOCUMENTS

EP           1764046 A2      3/2007
WO    WO-2007/049113 A1     5/2007

OTHER PUBLICATIONS

Yang et al., Comparative Evaluation of Handheld Robot-Aided Intraocular Laser Surgery, 2016, IEEE, p. 246-251 (Year: 2016).*
(Continued)

*Primary Examiner* — McDieunel Marc
(74) *Attorney, Agent, or Firm* — MARSHALL, GERSTEIN & BORUN LLP (57) ABSTRACT

A robotic working line and associated method for the production of cutting bodies for prosthetic surgery instruments starts with hollow untreated components and includes an automated three-dimensional laser cutting station with a first automated operator configured to pick up untreated components from a transport support and supply it to a laser cutting apparatus having a second automated operator provided with a laser cutting head that is configured to make both through holes and optional auxiliary apertures to obtain semi-finished components. An automated grinding station receives the semi-finished components and includes a third automated operator configured to place each of the semi-finished components in cooperation with one or more grinding tools in order to obtain ground components. An automated punching station includes a fourth automated operator to place each of said ground components in cooperation with a press device configured to perform a punching working on each hole.

9 Claims, 4 Drawing Sheets

(51) Int. Cl.
*B25J 9/16* (2006.01)
*B25J 11/00* (2006.01)
*B25J 15/00* (2006.01)

(52) U.S. Cl.
CPC ......... *B25J 9/1682* (2013.01); *B25J 11/0055* (2013.01); *B25J 11/0065* (2013.01); *B25J 15/0019* (2013.01)

(56) References Cited

U.S. PATENT DOCUMENTS

| | | | | |
|---|---|---|---|---|
| 10,758,714 | B2* | 9/2020 | Laby | A61M 25/0155 |
| 11,241,285 | B2* | 2/2022 | Viscardi | A61B 34/76 |
| 2003/0135219 | A1 | 7/2003 | Salyer et al. | |
| 2010/0331883 | A1* | 12/2010 | Schmitz | A61B 17/0218 606/279 |
| 2016/0136715 | A1 | 5/2016 | Liebel et al. | |
| 2020/0269022 | A1* | 8/2020 | Barrish | A61M 25/1025 |
| 2022/0040798 | A1* | 2/2022 | Lualdi | B23K 37/04 |

OTHER PUBLICATIONS

Hill et al., Robots and Tools for Remodeling Bone, 2019, IEEE, p. 184-198 (Year: 2019).*
Preising et al., A literature review: robots in medicine, 1991, IEEE, p. 13-22 (Year: 1991).*
Yang et al., Toward automated intraocular laser surgery using a handheld micromanipulator, 2014, IEEE, p. 1302-1307 (Year: 2014).*
Zhibiao et al., The Study on Fabrication of Solid Metal Microneedles Based on Optimized Process of Electrochemical Etching and Cutting, 2018, IEEE, p. 56-59 (Year: 2018).*
Zhou et al., Cutting, "by pressing and slicing", applied to robotic cutting bio-materials. I. Modeling of stress distribution, 2006, IEEE, p. 2896-2901 (Year: 2006).*
Kencana et al., Master and Slave Robotic System For Natural Orifice Transluminal Endoscopic Surgery, 2008, IEEE, p. 296-300, p. 296-300 (Year: 2008).*
Pereira et al., Hand-held robotic device for laparoscopic surgery and training, 2015, IEEE, p. 1-8 (Year: 2015).*
Search Report for IT 202000019411, dated May 10, 2021.

* cited by examiner fig. 1 fig. 4 fig. 5a fig. 5b fig. 6 fig. 7 fig. 8

ROBOTIC WORKING LINE FOR THE PRODUCTION OF CUTTING BODIES, CUTTING BODY AND RELATED WORKING METHOD

FIELD OF THE INVENTION

The present invention relates to a robotic working line for the production of cutting bodies for prosthetic surgery instruments, in particular cutting bodies suitable for milling/cutting or otherwise carrying out tissue removal processes in preparation for, or in the context of, prosthetic surgery, in this case in the orthopaedic field.

The invention also relates to a method of working said cutting bodies and to a cutting body thus made.

BACKGROUND

In general, prosthetic surgery instruments are known which are able to remove bone tissues by milling, cutting, abrasion and shaped to produce coordinated and conjugated bone sites suitable for the arrangement and implantation of related components of surgical prosthesis. Such instruments may be, for example, acetabular cutters, patellar cutters, glenoid cutters, rasps, broaches or similar or comparable instruments.

The aforementioned known instruments generally include an internally hollow cutting body, having a size related to the bone site to be made. On an external surface of the cutting body, a plurality of through holes are made, which are provided with sharp and protruding edges, able to carry out a mechanical excavation on the bone.

Currently, the production of the cutting body requires a plurality of machinery/apparatus both for the complexity of the cutting body and for the limits of the known machinery/apparatus.

Still in the state of the art, processing is necessary to create reference and treatment elements that, once the production process is finished, are eliminated. This leads to greater use of machinery/equipment, more time, and higher costs.

Typically, the cutting body is made from an untreated component in metallic material, for example, but not limited to, titanium or steel and is fed in sequence to a chip removal machine, a sharpening machine, a grinding machine, and a punching machine to then undergo appropriate washing treatments.

In particular, the chip removal machine is able to produce the aforementioned through holes, any grooves or also to remove edges or working frames. However, the through holes produced do not have an edge already suitable for the purpose of cutting and have to, therefore, be subjected to subsequent sharpening in a special sharpening machine. The sharpening machine operates on the entire edge of the hole, even in the segment not affected, in use, by the mechanical cutting action. This disproportionately weakens the external surface of the cutting body, also generating excessive waste and dust.

In addition, the need to sharpen the edges of the holes in a different machine than the one that produced them can lead to repositioning errors, excessive waste of time during the machine change, and therefore a decrease in productivity.

The through holes can also be produced using laser cutting apparatuses. However, such laser cutting apparatuses do not eliminate the need to sharpen the edges of the holes.

Another drawback of current production systems is that they require manual intervention by an operator in some of the processing steps. The need for human intervention implies long working times and the inability to ensure a good repeatability of the working results.

For example, the elimination of the burr formed during the cutting process is usually carried out by the operator by means of grinding devices; therefore, the consistency of the thicknesses of the processed materials is not guaranteed.

Furthermore, in current systems, the presence of the operator is usually required for the movement of the components worked by one machinery/apparatus to the other.

There is therefore a need to perfect a robotic working line for the production of cutting bodies for prosthetic surgery instruments that can overcome at least one of the drawbacks of the prior art.

In particular, a purpose of the present invention is to provide a robotic working line by means of which it is possible to reduce the number of machinery/apparatus necessary to carry out the workings.

One purpose is also to reduce the time required to carry out the workings.

Another purpose is to increase the repeatability of the machining, reducing as much as possible the need for an operator to perform the processing.

Another purpose of the invention is to realize a robotic working line by means of which it is possible to reduce the need for the intervention of an operator for the transport of the components being worked from one machine/apparatus to another.

A further purpose is to devise a working method for the production of cutting bodies for instruments for prosthetic surgery.

The Applicant has studied, tested and realized the present invention to overcome the drawbacks of the prior art, and to obtain these and further objects and advantages.

SUMMARY

The present invention is expressed and characterised in the independent claims. The dependent claims show other features of the present invention or variants of the main solution idea.

In accordance with the aforementioned purposes, a robotic working line for the production of cutting bodies for prosthetic surgery instruments which exceeds the limits of the prior art and eliminates the defects present therein is described.

According to embodiments, the robotic working line is able to produce the aforementioned cutting bodies from hollow untreated components having at least one external surface and an opposing internal surface.

The working line comprises an automated three-dimensional laser cutting station, an automated grinding station and an automated punching station.

The automated three-dimensional laser cutting station comprises a first automated operator and a laser cutting apparatus.

The first automated operator is configured to pick up each untreated component from a transport support.

The first automated operator is also configured to transfer the untreated component into the laser cutting apparatus.

Inside the laser cutting apparatus, a second automated operator provided with a laser cutting head is configured to make both through holes on the untreated component to define a cutting part of the cutting body and optional auxiliary apertures functional for the subsequent workings, to obtain a respective semi-finished component.

The automated grinding station is able to receive each semi-finished component arriving from the three-dimensional laser cutting station and comprises a third automated operator, configured to place the semi-finished component in cooperation with one or more grinding tools of the grinding station to obtain respective ground components.

The automated punching station is able to receive said ground components from the grinding station and comprises a fourth automated operator configured to place said ground components in cooperation with a press device one at a time.

The press device is configured to perform punching working on the holes from time to time to make an edge of each hole of the cutting part protrude.

In accordance with the above-mentioned purposes, a method for working cutting bodies for prosthetic surgery instruments and a cutting body thus made are also described.

BRIEF DESCRIPTION OF THE DRAWINGS

These and other aspects, features and advantages of the present invention will become clear from the following embodiment disclosure, given as a non-limiting example, with reference to the attached drawings in which:

FIGS. 2a, b, d, f, g are three-dimensional views of components being worked and of a cutting body according to embodiments;

FIGS. 2c, e are sectional views with respect to the planes IIc, IIe of details of the components of FIGS. 2b, d;

FIGS. 3a-b are three-dimensional views of cutting bodies according with embodiments;

FIG. 3c is a detail of the cutting body of FIG. 3b;

To facilitate understanding, identical reference numbers have been used, where possible, to identify identical common elements in the figures. It is to be understood that elements and features of an embodiment can be conveniently combined or incorporated into other embodiments without further clarification.

DETAILED DESCRIPTION

Reference will now be made in detail to the possible embodiments of the invention, one or more examples of which are shown in the attached figures by way of non-limiting example. The phraseology and terminology used herein is also for non-limiting exemplary purposes.

Embodiments described using the attached figures refer to a robotic working line 10 for the realization of cutting bodies 54 for prosthetic surgery instruments which can be by way of example acetabular cutters 54, patellar cutters, glenoid cutters, rasps 55, broaches 56 or similar or comparable tools.

Figures 2A, 2B, 2C, 2D, 2E, 2F, 2G, 3A, 3B, 3C:
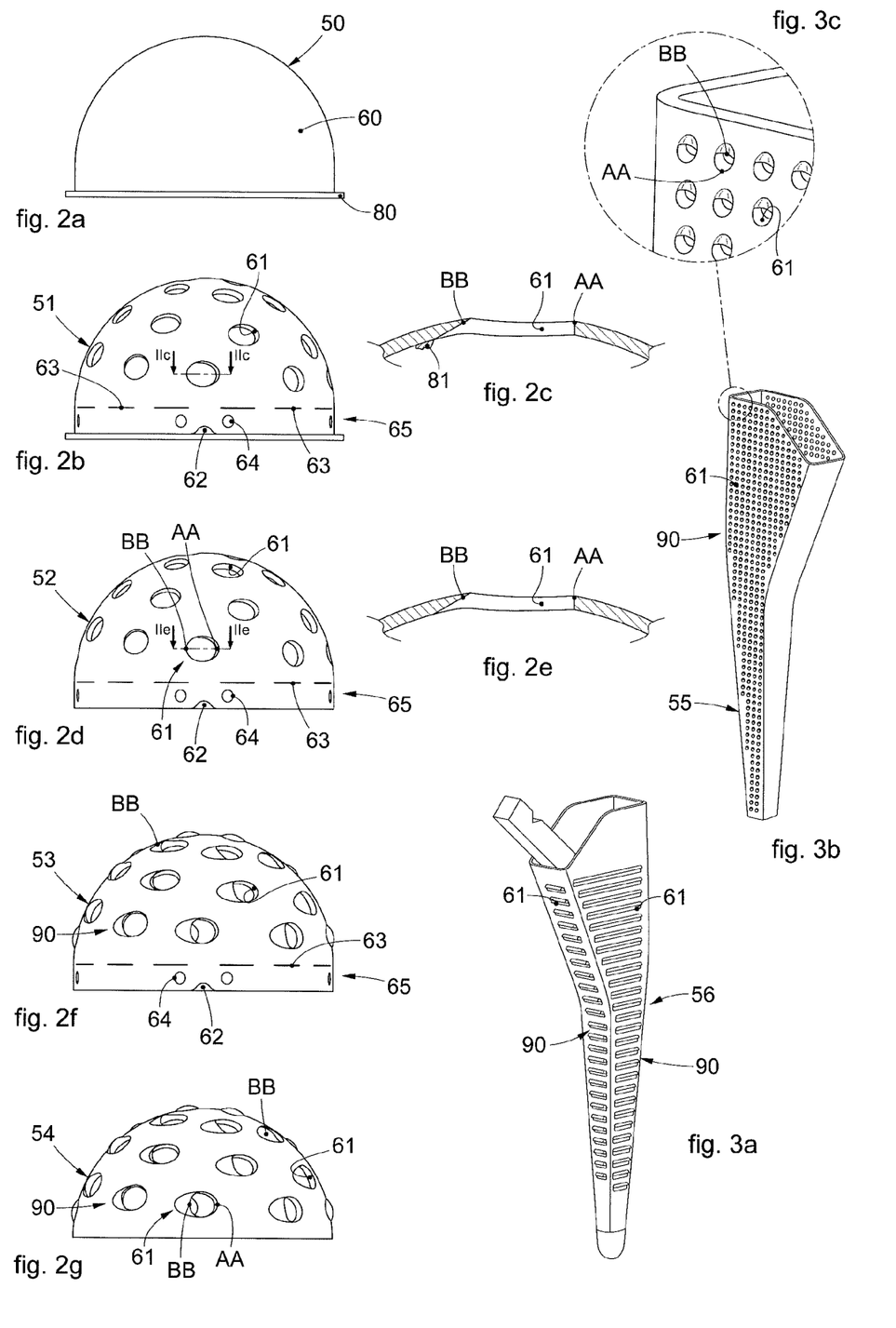

The cutting body 54 is obtained starting from a hollow untreated component 50 having at least one external surface 60 and an opposing internal surface 70 substantially continuous (FIG. 2a).

Untreated component 50 means an unfinished component obtained by a drawing, bending or the like operation to obtain an internal cavity identified by said internal surface 70. For example, the untreated component 50 can be obtained by drawing from a flat metal sheet and, as a result, have a concave, more or less complex shape.

Figure 7:
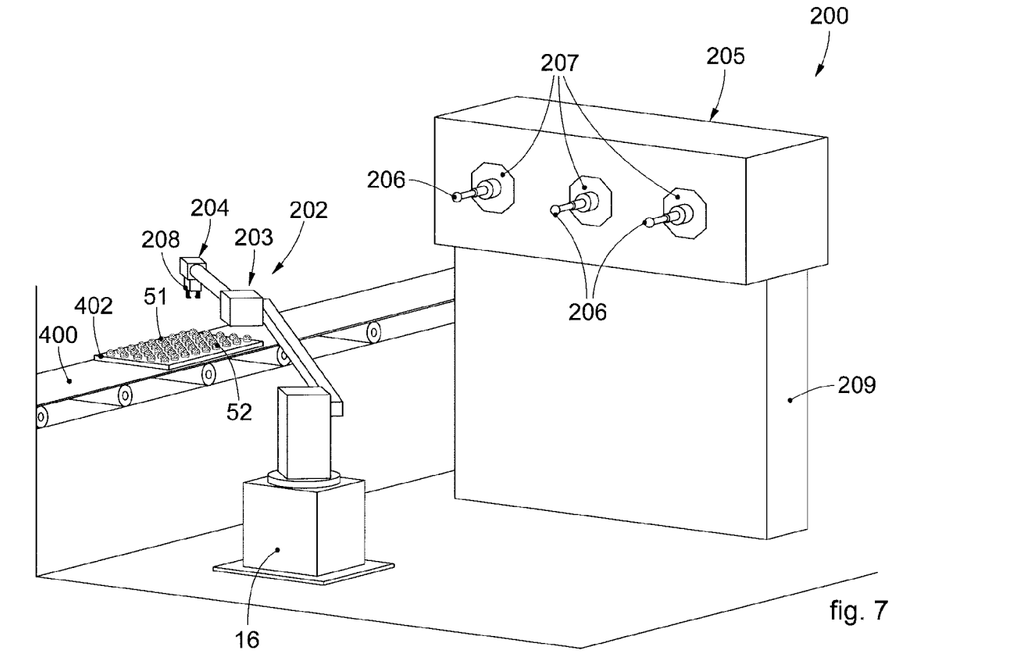
Figure 8:
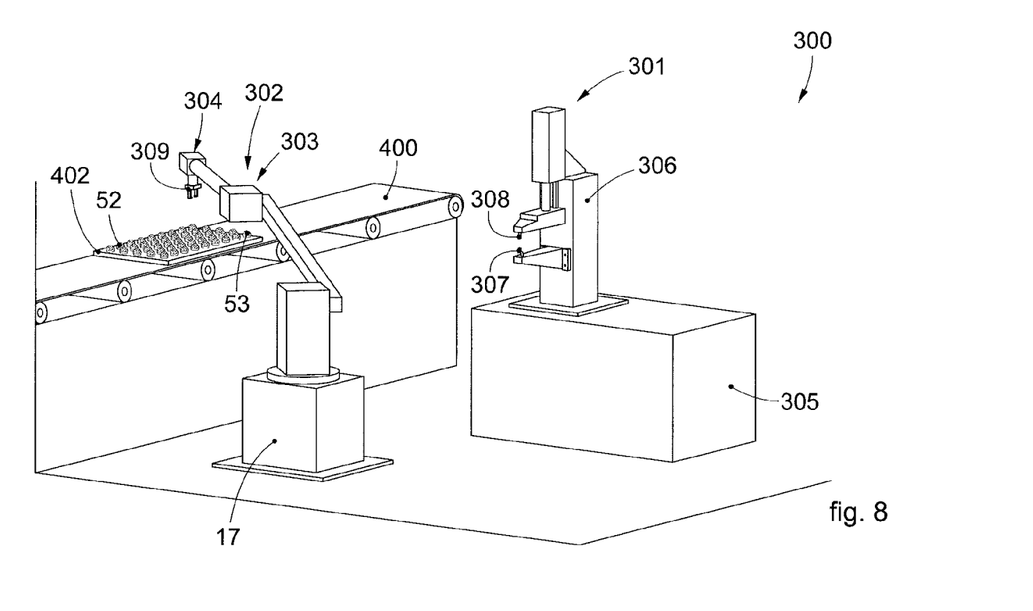

The working line 10 comprises an automated three-dimensional laser cutting station 100 (FIG. 6), an automated grinding station 200 (FIG. 7) and an automated punching station 300 (FIG. 8).

The laser cutting station 100 comprises a first automated operator 102, to pick up the untreated component 50 from a transport support 400, 402 and move a consequent semi-finished component 51 (FIG. 2b, c) obtained at the end of a three-dimensional laser cutting working.

Figure 6:
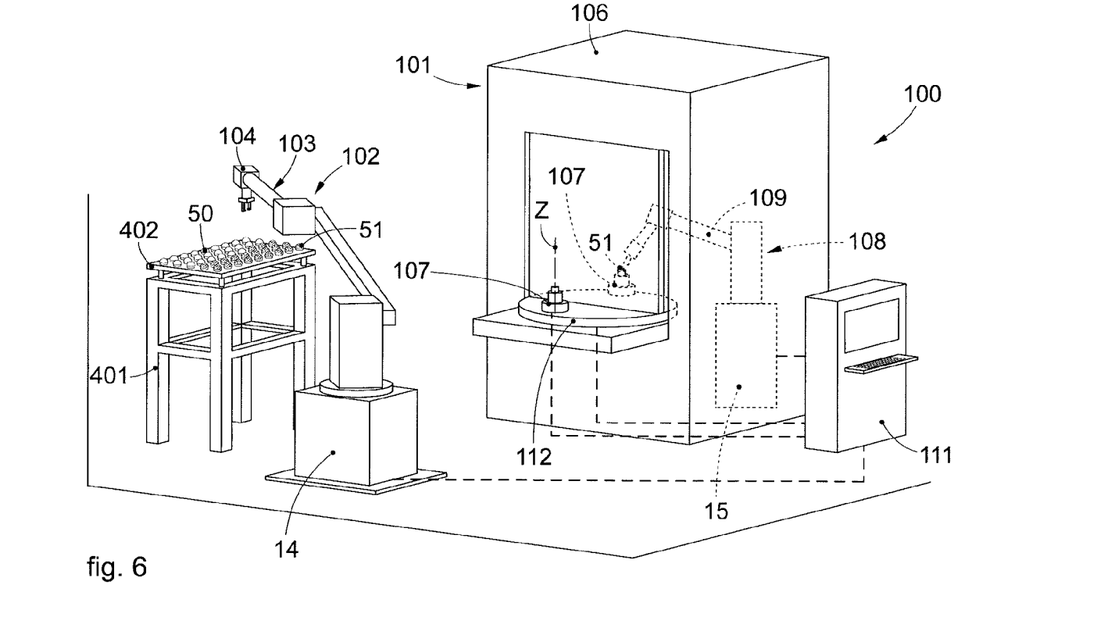
FIGS. 6-8 are three-dimensional views of automated stations of the working line of FIG. 1.

The laser cutting station 100 comprises a laser cutting apparatus 101 having a cutting chamber 106, at least one mandrel 107 mounted on movement systems 112 and a second automated operator 108.

The aforementioned movement systems 112 may comprise a support plane, such as a rotating plane or a plane movable in one or more directions or the like, and a movement device, such as an electric, pneumatic or similar motor, and may be able to move the mandrel 107 from a loading position of the untreated component 50 to a cutting position within the cutting chamber 106.

Inside the cutting chamber 106, a second automated operator 108 is positioned provided with a laser cutting head 110, configured to make both through holes 61 on the untreated component 50 able to define a cutting part 90 of said cutting body 54 and optional auxiliary apertures functional for the subsequent workings, to obtain a semi-finished component 51.

The aforesaid auxiliary apertures may be centring notches 62, perimeter slots 63 defining a pre-cut circumference, gripping holes 64 or the like and may be included at an auxiliary band 65.

The grinding station 200 comprises a third automated operator 202, configured to receive the semi-finished components 51 from the laser cutting station 100 and to manipulate them to place them in cooperation with one or more grinding tools 206 present in the grinding station 200 to obtain a ground component 52 starting from the semi-finished component 51.

The punching station 300 is able to receive the ground components 52 from said grinding station 200 and comprises an automatic press device 301 and a fourth automated punching operator 302.

The fourth automated operator 302 is configured to pick up, one at a time, the ground components 52 and to place them in cooperation with the press device 301.

The press device 301 is in turn configured to perform respective punching workings on the holes 61 to make an edge of each hole 61 of the cutting part 90 of the cutting bodies 54 protrude.

The aforementioned automated operators 102, 108, 202, 302 comprise a respective fixed base platform 14, 15, 16, 17 on which a respective robotic articulated arm 103, 109, 203, 303 is rotatably associated.

The robotic articulated arms 103, 109, 203, 303 comprise a plurality of elements rotatably articulated with respect to each other in succession, so as to allow the movement of the robotic articulated arms 103, 109, 203, 303 according to a number of degrees of freedom sufficient to allow the respective automated operators 102, 108, 202, 302 to carry out all the necessary manipulations and positioning.

In the present case, the robotic articulated arms 103, 203, 303 may be moved according to six degrees of freedom. This allows the pick up and/or positioning from/on the transport support 400, 402 respectively of the untreated component 50 or the components 51, 52, 53 and the subsequent manipulation operations without the intervention of an operator.

According to embodiments, the robotic articulated arms 103, 203, 303 are provided with a manipulation head 104, 204, 304 for picking up and positioning the components 50, 51, 52, 53 in a desired manner.

According to embodiments, the robotic articulated arm 109 of the second automated operator 108 is provided with a laser cutting head 110 movable according to at least four degrees of freedom, always remaining facing the external surface 60 of the untreated component 50 being worked.

The mandrel 107 may be configured to rotate about a vertical axis Z thereof. Advantageously, in this way the component 50 positioned on the mandrel 107 can be rotated by exposing its entire external surface 60 to the laser cutting head 110.

The laser cutting station 100 comprises a control unit 111 able to at least control the positioning of the untreated component 50, on the mandrel 107. The control unit 111 is also adapted at least to send an operating signal to the second automated operator 108 so that the laser cutting head 110 realizes the aforementioned holes 61 on the untreated component 50 being worked.

Each hole 61 (FIGS. 5*a-b*) is peripherally defined by a first segment, or edge, AA wherein the laser cutting head 110 is inclined by a first cutting angle $\alpha 1$ with respect to a reference plane P tangent to the external surface 60 passing through the centre C of the hole 61, and by a complementary second segment, or edge, BB, wherein the laser cutting head 110 is inclined by a second cutting angle $\alpha 2$ with respect to the aforementioned reference plane P.

Figure 5A:
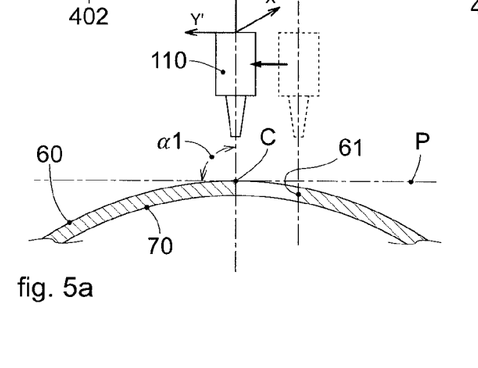
FIGS. 5a-b are sectional views of details of the component of FIG. 2b.
Figure 5B:
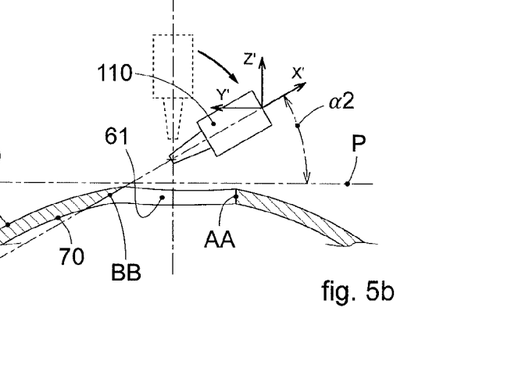

According to embodiments, the second angle $\alpha 2$ is different from the first angle $\alpha 1$, in particular is smaller.

In this way, the laser cutting head 20 allows to define, directly during the cutting process, a second already sharpened edge BB. This edge, or cutting edge, BB after punching working that will make it protruding, will be suitable for carrying out a mechanical excavation action on the bone.

The laser cutting station 100 disclosed herein allows, therefore, to reduce the working times, since such use of the laser cutting head 110 eliminates the need for subsequent sharpening workings of the edges.

It also allows, in shorter times than standard milling processes, to obtain a complex geometry such as that described.

Advantageously, the cut inclined in such a way as to define a sharp edge is made only on the sharp segment BB, allowing to limit the weakening of the structure of the cutting body 54 caused by a possible removal of material on the entire perimeter of the hole 61.

According to embodiments, the laser cutting head 110 may also be able to remove any perimeter edges, or flanges 80 (FIG. 2*a*) which may be present on the untreated component 50 due to the process by which it is made.

According to embodiments, the manipulation head 104 is able to pick up, at the end of the working, the finished semi-finished component 51 from the mandrel 107 and arrange it on the transport support 400, 402.

The grinding station 200 is configured to cooperate with the semi-finished component 51, exiting from the laser cutting station 100, to eliminate residual elements 81, or burrs, that may have formed during laser cutting processing of the cutting edge BB (FIGS. 2*c, e*).

In fact, since the laser engraves the external surface 60 of the component 50 with an angle not perpendicular to it, part of the material molten during cutting can solidify, in correspondence of the internal surface 70 in correspondence of the segment BB (FIG. 2*c*).

The solidified material, harder than the non-melted material, may damage or otherwise reduce the useful life of the punches 307 during subsequent punching working and should preferably be removed.

In a preferred embodiment, the grinding station 200 may comprise a grinding apparatus 205, provided with one or more grinding tools 206 and one or more drive means 207 adapted to drive the grinding tools 206.

The manipulation head 204 may comprise gripping devices 208 able to manipulate the semi-finished components 51 to place them in cooperation with said grinding tools 206.

The one or more grinding tools 206 can be grindstones, brushes and/or the like and are adapted to be rotated and to come into contact with the internal surface 70 of the semi-finished components 51 (FIGS. 2*b, c*), to remove the aforementioned residual elements of molten material.

In one embodiment, the grinding tools 206 have a grain that is gradually finer, to allow for an increasingly better grinding as the semi-finished component 51 moves from one grinding tool 206 to the next. For example, the first grinding tools 206 may be progressively finer grit grindstones and the last grinding tools 206 may be brushes.

In an alternative variant not shown, the manipulation head 204 may comprise the aforementioned grinding tools 206 and may be able to interface the grinding tools 206 with the internal surface 70 of the semi-finished components 51 to perform the grinding processing.

The grinding station 200 may further comprise a control unit 209 adapted at least to control the positioning of the semi-finished component 51 at one of the grinding tools 206 and at least to control the rotation of the one or more grinding tools 206. For example, it may be configured to send an operating signal to the grinding apparatus 205 to command the operation of the one or more drive means 207.

According to embodiments, the punching station 300 comprises a control unit 305 configured at least to command the automated operator 302 to pick up the ground components 52 one at a time from the transport support 400, 402.

The automated operator 302 may comprise, at the manipulation head 304, a gripping device 309 for gripping said ground components 52.

The control unit 305 may be configured at least to move the automated punching operator 302 and the press device 301 in a coordinated manner.

According to embodiments, the press device 301 has a device body 306, a punch 307, and a counter-punch 308.

The device body 306 may be able to support and move the punch 307 and the counter-punch 308. In particular, in the example shown in FIG. 8, the punch 307 is fixed and the counter-punch 308 is movable.

The control unit 305 may be configured to move the automated operator 302 so as to accompany the component 52 at the punch 307 and to position it on the punch 307 at the cutting edge BB of one of the holes 61.

The control unit 305 may further be configured to command the press device 301 to move the counter-punch 308 toward the punch 307 and the automated operator 302 to remain in the position described above until the counter-punch 308 contacts the component 52.

The control unit 305 may then be configured to command the automated operator 302 to move the component 52 in the same direction of movement as the counter-punch 308 toward the punch 307 until the punching working is complete.

Advantageously, in this way the component 52 does not undergo deformation at an area adjacent to the hole 61.

Components 50, 51, 52, 53 may be fed to/from the automated stations 100, 200, 300 manually by an operator, in a manual mode.

According to embodiments, the automated stations 100, 200, 300 comprise at least a warehouse 401 able to accommodate a plurality of the aforementioned components 50, 51, 52, 53.

Figure 4:
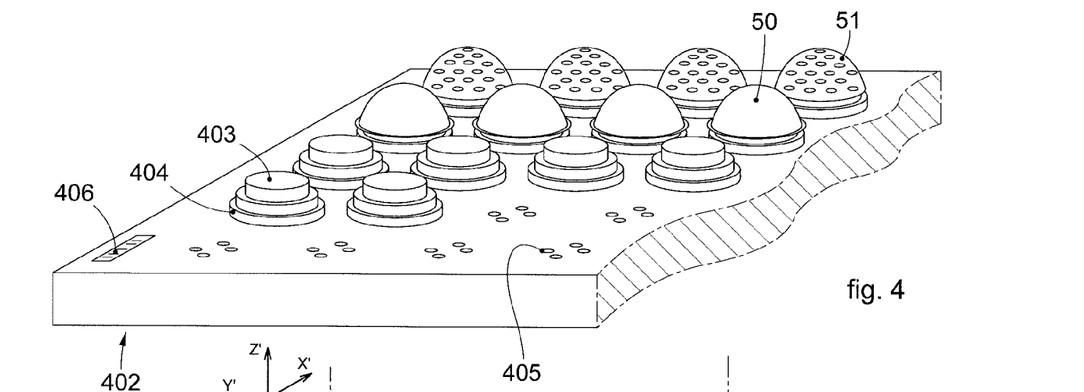
FIG. 4 is a three-dimensional view of untreated components being worked positioned on a transport support according to embodiments.

According to embodiments, the magazine 401 comprises at least one tray 402, or transport support 402, for the components 50, 51, 52, 53 (FIG. 4). The tray 402 can be disposed in support, i.e. associated above, to a support structure that can comprise vertical and horizontal support elements, so as to define a shape that resembles that of the frame of a table (FIG. 6).

A plurality of modular positioning elements 403 can be present on the tray, each of which is associated with the tray 402 through suitable positioning holes 405 defined on the latter.

Each modular positioning element 403 is able to position in a desired manner a respective component 50, 51, 52, 53. The modular positioning elements 403 may comprise adaptor elements 404, to support components 50, 51, 52, 53 of different dimensions.

For example, in the case of components 50, 51, 52, 53, having a spherical cap shape, intended for the production of acetabular cutters, the modular positioning elements 403 can comprise a central body of cylindrical shape projecting from the tray 402 with which a plurality of rings 404 having gradually decreasing diameter can be associated.

According to embodiments, the tray 402 may be associated with an RFID radio frequency type identification label 406, on which information relating to the components 50, 51, 52, 53 supported by it is stored. The aforementioned information may relate to the type, dimension or size of the components 50, 51, 52, 53, as well as an identification of the successful processing or similar information.

According to possible embodiments, a respective identification label 406 can be associated with each position defined on the tray 402. A respective identification label 406 may also be associated with the modular positioning elements 403 and/or the adaptor elements 404.

In an alternate embodiment, the automated stations 100, 200, 300 may be connected to each other in an automatic mode, via a transport line 400.

The components 50, 51, 52, 53 can be powered in an automated manner to/from the automated stations 100, 200, 300 by the aforementioned transport line 400 that interfaces with the input and/or output of each automated station 100, 200, 300, respectively.

In this way, it is not necessary for an operator to move the components 50, 51, 52, 53 from one automated station to another.

The transport line 400 allows the movement of the components 50, 51, 52, 53, in a unique direction of advancement, sequentially crossing the aforementioned automated stations 100, 200, 300. The transport line 400 may comprise one or more transport devices, e.g., belt conveyors, band conveyors, or the like.

Figure 1:
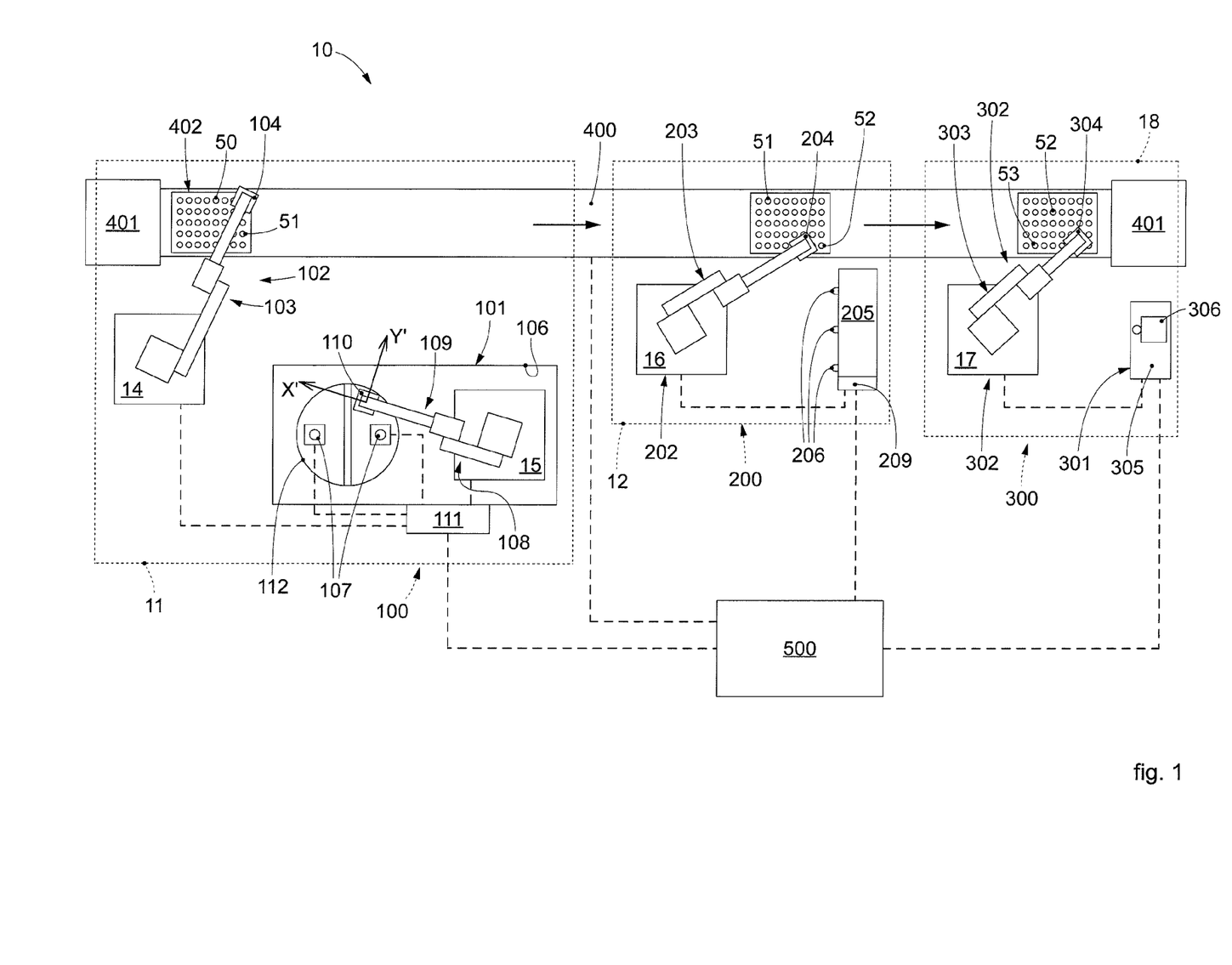
FIG. 1 is a schematic plan view of a robotic working line according to embodiments.

As shown in FIG. 1, a respective operating perimeter 11, 12, 13 of the laser cutting stations 100, grinding stations 200, punching stations 300 may be defined. In the case of a line 400 comprising a single transport device, this enters the operating perimeter 11, 12, 13 of the station 100, 200, 300 where, inside the station 100, 200, 300, there are respective specific working operating zones in which at least one respective processing step is completed by at least one of the aforementioned automated operators 102, 108, 202, 302.

In further embodiments not illustrated, a plurality of transport devices are provided, each of which may be interrupted at the operating perimeter 11, 12, 13.

The transport line 400 can cooperate with the trays 402, for containing the components 50, 51, 52, 53. The trays 402 can have, for example on their sides, specific gripping elements for being manipulated and moved in an automated manner, for example, towards the next automated station 100, 200, 300.

The transport line 400 may cooperate with at least one warehouse 401 able to accommodate one or more trays 402, positioned for example at the beginning and/or end of the transport line 400. The magazine can be adapted, in this case, to accept, for example by an operator, the one or more trays 402 of the untreated components 50 or to receive the trays 402 of the punched components 53 from the transport line 400 pending pick up by the operator.

In an embodiment not shown in the figures, the transport line 400 may be able to operate as a transport support 400 for the components 50, 51, 52, 53. The transport line 400 may in this case include a plurality of modular positioning elements 403 to which adaptor elements 404 may possibly be associated, similar to what is described above. Respective identification labels 406 may be associated with the modular positioning elements 403 and/or the adaptor elements 404.

The components 50, 51, 52, 53 may be positioned on said modular positioning elements 403, randomly or at a predefined position.

In a preferred embodiment, the untreated components 50 may be positioned randomly, but the semi-finished components 51 may be positioned repeatably, with the centring notch 62 in a predetermined position. In this way, the automated punching operator 302 can know the positioning map of the holes 61 in advance.

As an alternative example, all components 50, 51, 52, 53 may be positioned randomly, and the location of the positioning map of the holes 61 is by specially arranged devices, such as optical devices, cameras, sensors, or the like.

In a further alternative embodiment not illustrated, the stations 100, 200, 300 may be connected to each other in a semi-automatic mode, for example by robotic devices for transporting the components from one station to the next.

According to embodiments, the working line comprises a central control unit 500 configured to coordinate the control units 111, 209, 305 and possibly the transport line 400.

According to an alternative variant not illustrated, the central control unit 500 is configured to directly control the automated stations 100, 200, 300 and possibly the transport line 400.

Embodiments described herein relate to a manufacturing method for manufacturing cutting bodies 54 for prosthetic surgery instruments.

According to embodiments, the method includes performing a first three-dimensional laser cutting working, a second grinding processing and a third punching working.

The method may comprise:
picking up the untreated component 50 from a transport support 400, 402;
transferring the untreated component 50 to a cutting chamber 106 by means of a second automated operator 108;
making on the untreated component 50 both holes 61 able to define a cutting part 90 of said cutting body 54 and optional auxiliary apertures 62, 63, 64 functional to the subsequent working, to obtain a semi-finished component 51;

receiving said semi-finished components 51 in an automated grinding station 200 by means of a third automated operator 202;

manipulating said semi-finished components 51 to place them in cooperation with one or more grinding tools 206 present in said grinding station 200 to obtain a ground component 52 from said semi-finished component 51;

receiving said ground components 52 from said grinding station 200 in an automated punching station 300;

picking up said ground components 52 one at a time and placing them in cooperation with a press device 301 configured to perform punching working on each hole 61 from time to time to make an edge of each hole 61 of the cutting part 90 of the cutting bodies 54 protrude.

According to one embodiment, the method includes moving the automated operators 102, 202, 302 so as to pick up the component 50, 51, 52 from the conveyor support 400, 402 at the beginning of the working and reposition the component 51, 52, 53 on the transport support 400, 402 at the end of the working.

According to a preferred embodiment, the method includes that the first automated operator 102 positions at the modular positioning elements 403 the semi-finished components 51 with an orientation known to the cutting machine, for example in reference to a centring notch 62.

According to an alternative variant, the semi-finished components 51 are randomly oriented and the orientation is recognized by a system for the recognition of the position assumed by the semi-finished component 51, such as for example an optical system, or an electrical conductivity meter system or the like, for example by recognizing the position of the centring notch 62.

Advantageously, it is thus possible to know the position and orientation of the holes 61 for the punching working.

According to an embodiment, the method provides, during grinding processing, to position the semi-finished component 51 at a grinding tool 206 arranged in a fixed position and command the rotation of the grinding tool 206.

According to an alternative variant, the method involves grinding processing by grinding tools 206 included in a manipulation head 204 of the third automated operator 202.

According to an embodiment, the method includes, during processing, moving the automated operator 302 so as to accompany the component 52 at the counter-punch 308 and to position it on the counter-punch 308 at a cutting edge BB of one of the holes 61.

The method may further provide for the counter-punch 308 to be moved toward the punch 307 and the automated operator 302 to be maintained in the position described above until the counter-punch makes contact with the component 52.

It can then provide for moving the component 52, by means of the automated operator 302, in the same direction of movement of the counter-punch 308 towards the punch 307 until the punching working is completed.

The method can involve repeating the steps described for all the holes 61 (FIG. 2*f*).

According to an embodiment, the method therefore envisages sending the punched component 53 (FIG. 2*f*) to the subsequent manual removal operations of the auxiliary band 65, for example along the pre-cut circumference defined by the perimeter slots 63, medical type finishing, such as polishing, washing, sterilization or the like, and control to obtain the finished cutting body 54 (FIGS. 2*g*, 3*a-c*).

Embodiments described herein relate to a cutting body 54 made by a robotic working line 10 and in accordance with the working method according to the invention, having at least one cutting part 90 delimited by an external surface 60 and an opposing internal surface 70.

According to embodiments, said cutting part 90 is provided with a plurality of holes 61 passing from said external surface 60 to said internal surface 70, wherein each hole 61 has a first edge AA and a complementary second edge BB having different inclinations.

Each of said holes 61 is peripherally defined by the first edge AA which has an inclination of a first cutting angle $\alpha 1$ with respect to a reference plane P tangent to the external surface 60 passing through the centre C of the hole 61, and by a second complementary edge BB which has an inclination of a second cutting angle $\alpha 2$ with respect to said reference plane P, smaller than said first cutting angle $\alpha 1$.

It is clear that modifications and/or additions of parts or steps can be made to the robotic working line 10, to the working method and to the cutting body 54 described so far, without departing from the scope of the present invention as defined by the claims.

In the following claims, the references in parentheses have the sole purpose of facilitating reading and must not be considered as limiting factors as regards the scope of protection underlying the specific claims.

The invention claimed is:

1. A robotic working line for the production of cutting bodies for prosthetic surgery instruments starting from hollow untreated components, wherein said robotic working line comprises in succession:

an automated three-dimensional laser cutting station with a first automated operator configured to pick up said untreated components from a transport support and supply it to a laser cutting apparatus in which a second automated operator provided with a laser cutting head is configured to make both through holes and also optional auxiliary apertures to obtain corresponding semi-finished components;

an automated grinding station able to receive said semi-finished components comprising a third automated operator configured to place each of said semi-finished components in cooperation with one or more grinding tools in order to obtain respective ground components; and an automated punching station comprising a fourth automated operator able to place each of said ground components in cooperation with a press device configured to perform a punching working on each hole.

2. The robotic working line as in claim 1, wherein said laser cutting station comprises a control unit able at least to command the positioning of the untreated component on a mandrel and to send an operating signal to the second automated operator so that the laser cutting head makes at least one hole on the untreated component being worked.

3. The robotic working line as in claim 1, wherein the grinding station comprises one or more drive means able to drive said grinding tools, and in which said third automated operator comprises gripping devices able to handle the semi-finished components to place them in cooperation with said grinding tools.

4. The robotic working line as in claim 1, wherein said grinding station comprises a control unit able at least to command the positioning of said semi-finished component in correspondence with a grinding tool.

5. The robotic working line as in claim 1, wherein said punching station comprises a control unit configured at least to command the automated punching operator to pick up, one at a time, the ground components from the transport support and to move the automated punching operator and the press device in a coordinated manner.

6. The robotic working as in claim 1, wherein said robotic working line comprises a transport line which connects said automated stations for the automated feed of said components to/from the automated stations, said transport line interfacing respectively with the entry and/or the exit of each automated station (100, 200, 300).

7. The robotic working as in claim 1, wherein said robotic working line comprises a central control unit configured to coordinate the control units of the respective automated stations and possibly the transport line.

8. A working method to produce cutting bodies for prosthetic surgery instruments starting from hollow untreated components, wherein said robotic working line provides to:

picking up in an automated three-dimensional laser cutting station each of said untreated components from a transport support by means of a first automated operator and transfer it to a laser cutting apparatus in which a second automated operator provided with a laser cutting head makes on said untreated component both through holes able to define a cutting part and also optional auxiliary apertures functional for the subsequent workings, to obtain respective semi-finished components;

transferring said semi-finished components to an automated grinding station where a third automated operator places each of said semi-finished components in cooperation with one or more grinding tools in order to obtain respective ground components; and transferring said ground components to an automated punching station where a fourth automated operator places each of said ground components in cooperation with a press device which performs a punching working on each hole to make one edge of each hole of said cutting part protrude.

9. The working method as in claim 8, wherein said robotic working line provides, during the grinding processing, to position the said semi-finished component in correspondence with a grinding tool disposed in a fixed position by means of the third automated operator.

* * * * *